United States Patent [19]

Knoll et al.

[11] 3,954,986

[45] May 4, 1976

[54] PHARMACEUTICAL COMPOSITION HAVING SYNERGISTIC ANALGESIC ACTIVITY

[75] Inventors: József Knoll; Zsuzsanna Fürst; Zoltán Mészáros; Péter Szentmiklósi; Ágoston David; István Hermecz; Attila Mándi, all of Budapest; Rezsö Bognár; Sándor Makleit, both of Debrecen; Gyula Valovics, Tiszavasvari; László Szlávik, Tiszavasvari; Sándor Nagy, Tiszavasvari, all of Hungary

[73] Assignee: Chinoin Gyogyszer es Vegyeszeti Termekek Gyara RT., Budapest, Hungary

[22] Filed: Nov. 14, 1973

[21] Appl. No.: 415,749

[30] Foreign Application Priority Data
Dec. 19, 1972 Hungary............................. CI 1322

[52] U.S. Cl................................. 424/251; 424/260
[51] Int. Cl.$^2$............... A61K 31/505; A61K 31/485
[58] Field of Search........................... 424/260, 251

[56] References Cited
FOREIGN PATENTS OR APPLICATIONS
1,209,946  10/1970  United Kingdom OTHER PUBLICATIONS
Bognar et al., Acta Chim. Acad. Sci., Hung. 58, pp. 203–205, (1968).

Primary Examiner—Stanley J. Friedman
Attorney, Agent, or Firm—Karl F. Ross; Herbert Dubno

[57] ABSTRACT
An analgesic substitute for morphine comprising the synergistic combination of azidomorphine or azidocodeine with a pyrimidazolium.

1 Claim, No Drawings

PHARMACEUTICAL COMPOSITION HAVING SYNERGETIC ANALGETIC ACTIVITY

The present invention relates to pharmaceutical compositions having synergistic analgesic activity and a process for the preparation thereof.

For the relief of postoperational pain and in the case of cancer patients in an advanced stage of the disease morphine and its derivatives are the most frequently used efficient analgesics. It is a well known fact, however, that in patients treated with morphine, the harmful side-effects, e.g. respiratory depression, tolerance and dependence develop in a relatively short time. The patient gets used to morphine and rapidly rising doses are required to obtain an equianalegesic effect; tolerance or dependence develops and the patient is in permanent need of the euphorizing effect of morphine. Another disadvantage of morphine is the fact that it is practically ineffective on oral application.

All the analgesics suited for the treatment of unbearable pain (e.g. cancer, postoperative, infarction, lithiases, etc.) are liable to induce the development of tolerance on chronic administration and their withdrawal produces severe — often fatal — somatic and psychic symptoms (physical and psychic dependence). It is generally accepted (Martin, 1967, Pharm. Rev. 19, 463) that the appearance of tolerance and dependence necessarily accompany the action of the morphine type drugs on the analgesic receptors. An analgesic equipotent to morphine, but devoid of its narcotic side-effects, has for long been needed in clinical practice.

According to the present invention there is provided a pharmaceutical composition of synergistic analgesic activity comprising at least one azidocompound of the formula (I)

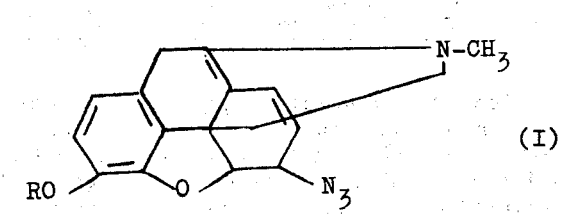

(I)

or a salt thereof (wherein R is hydrogen, methyl, ethyl, acetyl or morpholino-methyl) and at least one compound selected from the group consisting of compounds of the formula (II)

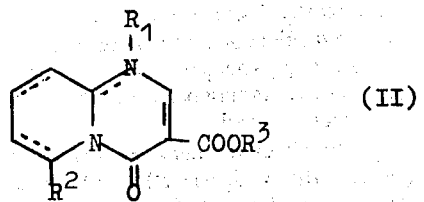

(II)

(wherein $R^1$, $R^2$ and $R^3$ are hydrogen or lower alkyl and the dotted lines represent optionally hydrogenated bonds) and pharmaceutically acceptable salts and quaternary salts thereof and analgesic butyrophenone derivative, in admixture with suitable inert solid or liquid carriers or diluents.

The present invention is based on the recognition that some homopyrimidazole derivatives and/or analgesic butyrophenone derivatives potentiate the analgesic action of the azido-compounds of the formula (I) to a significant extent while having an advantageous influence on their other properties. A further advantage resides in the fact that the combinations according to the present invention are devoid of narcotic side effects.

The compositions according to the present invention may contain preferably azidomorphine, azidocodeine, azidoethylmorphine, azidoacetyl-morphine or azido-morpholinomethyl-morphine as the compound of the formula (I). These compounds may used in the form of the free base or as pharmaceutically acceptable acid addition salts. It is preferred to use the bitartarate salts which possess advantageous solubility properties.

In the compounds of the formula (II) the alkyl groups may be straight or branched chained and contain 1–6, preferably 1–4 carbon atoms (e.g. methyl, ethyl, n-propyl, isobutyl, etc.) The salts and quaternary salts of the compounds of the formula (II) may contain any pharmaceutically acceptable anion (e.g. inorganic anions, such as nitrate, chloride, bromide or sulphate anion; and organic anions e.g. methylsulphate, ethylsulphate etc.). A particularly preferred representative of the compounds of the formula (II) is the 1,6-dimethyl-3-carbethoxy-4-oxo-6,7,8,9-tetrahydro-homopyrimidazolium-methosulphate.

As the butyrophenone component any known analgesic butyrophenone derivative may be used. As an advantageous example of these compounds the 4'-fluor-4-{4-[2-oxo-2,3-dihydrobenzimidazolyl-(1)]-1,2,3,6-tetrahydro-pyridyl-(1)}-butyrophenone is mentioned.

Preferred compositions according to the present invention contain azidomorphine, azidocodeine, or the bitartarate thereof as compound of the formula (I) and 1,6-dimethyl-3-ethoxycarbonyl-4-oxo-6,7,8,9-tetrahydro-homopyrimidazolium-methosulphate as compound of the formula (II).

The active ingredients of the synergistic combinations of the present invention are known. The azido compounds of the formula (I) and the preparation thereof are described by R. Bognár and S. Makleit: Acta Chim, Acad. Sci. Hung. 58, 203 (1968). The homopyrimidazole derivatives of the formula (II) and salts and quaternary salts thereof and also the preparation of these compounds is described in our Austrian Pat. Nos. 294 107 and 296 996. The analgesic butyrophenone derivatives are also well known from the prior art.

The relative amount of the active ingredients in the combination according to the present invention may vary between wide ranges. It may be stated that the composition may contain about 20–1000 parts by weight of a compound of the formula (II) related to 1 part by weight of an azido-compound of the formula (I).

The pharmaceutical compositions of the formula (I) may be finished in dosage forms suitable for oral or parenteral administration. The oral forms may be tablets, capsules, pills, coated pills etc. While the parenteral dosage forms may be injectable preparations, powder ampouls etc.

the pharmaceutical combinations of the present invention comprising azidocodeine or a salt thereof as compound of the formula (I) are suitable for oral administration (tablets, capsules) too. This oral dosage form is particularly advantageous, since in the clinical practice of analgetics of morphine type it enables the elimination of the injection treatment, being very unconfortable and painful, for the first time. The said oral composition comprises preferably about 20–100 parts by weight, particularly preferably 40 parts by weight of a compound of the formula (II) calculated on 1 part by weight of azidocodeine or the bitartarate thereof. A highly preferred embodiment of the present invention is a tablet or capsule comprising about 150–250 mg., particularly 200 mg. of 1,6-dimethyl-3-carbethoxy-4-oxo-6,7,8,9-tetrahydrohomopyrimidazolium-methosulphate and 2.5–10 mg., preferably 5 mg. of azidocodein or the bitartarate thereof.

The parenteral compositions acording to the present invention contain preferably 100–1000 parts by weight of a compound of the formula (II) related to 1 part by weight of an azidocompound of the formula (I). A very preferred embodiment of the present invention if a parenteral composition (injectable solution, powder ampoule) comprising about 150–500 mg. of 1,6-dimethyl-3-carbethoxy-4-oxo-6,7,8,9-tetrahydro-homopyrimidazolium-methosulphate and about 0.2-0.5 mg. of azidomorphine-bitartarate.

The synergetic compositions of the present invention may be prepared by methods of pharmaceutical industry known per se.. The compositions for oral administration may be prepared by admixing the active ingredient with inert non-toxic carriers or diluents (e.g. cellulose, silicic acid, stearine, polyvinylpyrrolidone, talk, starch, etc.). The said compositions may also contain the well known additives (e.g. emulsifying, suspending agents, dyes, salts for controlling the osmotic pressure, buffers, etc.).

The parenteral compositions of the present invention may be prepared in aqueous or non-aqueous medium. The non-aqueous preparations may be prepared in propylene glycol, polyethylene glycol or any other suitable solvents. Powder, ampoules may be prepared preferably by introducing homopyrimidazole derivative of the formula (II) into a powder ampoule, dissolving an azidocompound of the formula (I) in distilled water or in a suitable non-aqueous medium, in a solvent ampoule and dissolving a homopyrimidazole derivative of the powder ampoule before us in the content of the solvent ampoule.

The pharmaceutical compositions may also be finished in other suitable dosage unit forms according to known methods of pharmaceutical industry.

The synergistic analgesic activity of the combinations according to the present invention is shown and verified by the following comparative tests.

The preparation forming the object of our invention displays synergism regarding its analgetic effect. The activity of the combination significantly surpasses that of the individual components, consequently equianalgesic effect ($ED_{50}$) is obtained by much lower doses than that of the azidocompounds of the formula (I).

Synergism is measured with the help of the algolytic test (Knoll J.: Animal and Clinical Pharm. Techn. in Drug. Ev. /1967/ 305–321). The test is suited only for the demonstration of the effect of major analgesics. The test compound is administered in various doses. Analgesia is evaluated on the ground of the following scale:

SCORES

Violent

Persistent vehement attempts to move: persistent crying

Intense

Periodic attempts to move; persistent crying

Slight

Occasional faint stirring, occasional crying on irritation

Very slight

No stirring, occasional crying on strong irritation

None

Remains still and keeps silent

The results obtained are summarized in the following table:

| Dose mg/kg | MZ - 144 Mode of appl. | Pretr. time | Dose mg/kg | Azidocodeine Mode of appl. | Pretr. time | Pain units |
|---|---|---|---|---|---|---|
| — | — | — | 30 | p.o. | 1 hour | 87 |
| — | — | — | 45 | p.o. | 1 hour | 38 |
| — | — | — | 60 | p.o. | 1 hour | 30 |
| 300 | p.o. | 1 hour | — | — | — | 75 |
| 300 | p.o. | 1 hour | 30 | p.o. | 1 hour | 57 |
| 300 | p.o. | 1 hour | 45 | p.o. | 1 hour | 0 |
| 300 | p.o. | 1 hour | 60 | p.o. | 1 hour | 0 |

It appears from the diagram plotted on the basis of the above data the $Ed_{50}$ of azidocodeine in the algolytic test is 32 mg./kg., while that combination of azidocodeine and MZ-144 is 12 mg./kg. p.o. which clearly proves the synergism between the two compounds.

MZ 144 means 1,6-dimethyl-3-carbethoxy-4-oxo-6,7,8,9-tetrahydro-homopyrimidazolium-methosulphate.

Further advantage of the synergistic preparation is the prolongation of the duration of the effect. A modified "hot plate test" was used in the experiments (Pórszász, J. and Herr, F.: Kisérl. Orvostud. /1950/ 2292). According to the results obtained in the test, the effect of azidocodeine lasts for 2–2.5 hours, while the duration of the effect of the combination azidocodeine + 1,6-dimethyl-3-carbethoxy-4-oxo-6,7,8,9-tetrahydro-homopyrimidazole-methosulphate is 3.5–4 hours.

Following synergism of the effect, the dose of the individual components of the preparation can be substantially reduced.

In animal experiments it was found that the synergism in the analgetic effect of the compounds is not accompanied by addition of the side-effect, moreover the preparation referred to in the invention is practically devoid of side-effects. Thus, the combination containing azidocodeine and 1,6-dimethyl-3-carbethoxy-4-oxo-6,7,8,9-tetrahydro-homopyrimidazolemethosulphate in 1:40 proportion, according to clinical experience fails to depress respiration.

The analgesic affect was measured by the algolytic test developed and later modified by Knoll (Knoll, J.: Animal and Clinical Pharm. Techn. in Drug. Ev., 305–321). The method is a model of operational pain and as that is suited only for the demonstration of major analgesic effect. The test is based on the observation that 10 mg./kg. morphine administered i.v. to rats, produces complete analgesia so that the animal endures laparatomy without pain response and muscular straining and does not show the slightest sign of prostration following the operation. Only complete relief of pain was taken as analgesic effect. Each dose was administered to a group of 10 rats and the animals displaying complete analgesia were expressed in percent of the controls. This was considered as the measure of analgesia.

The synergistic effect of the preparation forming the object of the present invention was determined on the basis of the combination containing azidomorphine and 1,6-dimethyl-3-carbethoxy-4-oxo-6,7,8,9-tetrahydro-homopyrimidazole-methylsulphate. The combination of per se ineffective doses of the components (0.062 mg./kg. azidomorphine + 100 mg./kg. s.c. homopyrimidazole derivative) produced a 80 % effect, which means that the combination produced complete analgesia in 80% of the animals.

The advantageous synergism observed in the analgesic effect is not accompanied by the increase of toxicity.

Toxicity of combination was determined in Wister rats of both sexes weighing 120–150 g. $LD_{50}$ values were calculated by the Litchfield-Wilcoxon method. Toxicity of a combination containing 75% of the $LD_{50}$ of two components was determined. The death rate in the population was 50 %, i.e. lower than expected, which means that synergism in the analgesic effect of the compounds is not accompanied by synergism in toxicity.

Further details of the present invention are to be found in the following Examples without limiting the scope of the invention to the Examples.

EXAMPLE 1

Tablets having the following compositions are prepared by admixing the components and pressing the mixture to tablet form.

| | |
|---|---|
| Azidocodeine | 5 mg. |
| 1,6-dimethyl-3-carbethoxy-4-oxo-6,7,8,9-tetrahydro-homopyrimidazolium-methosulphate | 200 mg. |
| Titandioxide | 3 mg. |
| Betaine hydrochloride | 3 mg. |
| Colloidal silicic acid | 13 mg. |
| Polyvinyl pyrrolidone | 15 mg. |
| Stearine | 26 mg. |
| Crystalline cellulose | 76 mg. |

EXAMPLE 2

500 mg. of 1,6-dimethyl-3-carbethoxy-4-oxo-6,7,8,9-tetrahydro-homopyrimidazolium-methosulphate are introduced in a powder ampoule. In a solvent ampoule 0.5 mg. of azidomorphine-bitartarate are dissolved in 5 ml. of distilled water. Before use the homopyrimidazolium-derivative of the powder empoule is dissolved in the content of the solvent ampoule. The composition is suitable for intravenous administration. In use at surgical intervention the proposed dose in 1 ampoule.

EXAMPLE 3

A parenteral preparation having the following composition is prepared:

| | |
|---|---|
| 1,6-dimethyl-3-carbethoxy-4-oxo-6,7,8,9-tetrahydro-homopyrimidazolium-methosulphate | 200 mg. |
| Azidomorphine-bitartarate | 0.2 mg. |
| Distilled water q.s. | 2 ml. |

The injectable solution thus obtained is filled into ampoules.

EXAMPLE 4

A known aqueous parenteral composition is prepared having the following composition:

| | |
|---|---|
| 1,6-dimethyl-3-carbethoxy-4-oxo-6,7,8,9-tetrahydro-homopyrimidazolium-methosulphate | 150 mg. |
| Azidomorphine-bitartarate | 0.5 mg. |
| Propylene glycol | 0.66 ml. |
| Polyethylene glycol | 0.66 ml. |
| Cellosolve | 0.66 ml. |

The injectable solution thus obtained is filled into ampoules. The solution is very stable; during storage at 20°C for 5 years the decomposition is but a few percent.

What we claim is:
1. In an analgesic composition, the synergistic combination of 300 parts by weight of 1,6-dimethyl-3-carbethoxy-4-oxo-6,7,8,9-tetrahydro-homopyrimidazolium-methosulphate with substantially 45 to 60 parts by weight of azidocodeine.

* * * * *